United States Patent [19]
Denis et al.

[11] Patent Number: 5,773,642
[45] Date of Patent: Jun. 30, 1998

[54] PROCESS FOR THE PREPARATION OF CARBOXYLIC ACIDS OR THE CORRESPONDING ESTERS IN THE PRESENCE OF A SOLUBLE CATALYST BASED ON IRIDIUM AND IODIDES

[75] Inventors: Philippe Denis, Decines; Dominique Nobel, Salindres; Robert Perron, Charly; Philippe Perrona, Lyon; Joël Schwartz, Caluire, all of France

[73] Assignee: Acetex Chimie, Paris La Defense 2, France

[21] Appl. No.: 737,507

[22] PCT Filed: May 15, 1995

[86] PCT No.: PCT/FR95/00625

§ 371 Date: May 14, 1997

§ 102(e) Date: May 14, 1997

[87] PCT Pub. No.: WO95/31426

PCT Pub. Date: Nov. 23, 1995

[30]     Foreign Application Priority Data

May 13, 1994  [FR]  France .................................. 94 05896
Oct. 21, 1994  [FR]  France .................................. 94 12712

[51] Int. Cl.$^6$ ............................ C07C 67/36; C07C 51/12
[52] U.S. Cl. ........................... 560/232; 562/517; 562/519; 562/520

[58] Field of Search ............................ 560/232; 562/517, 562/519, 520

[56]         References Cited

U.S. PATENT DOCUMENTS

| 4,482,497 | 11/1984 | Rizkalla ................................. 260/413 |
| 4,681,707 | 7/1987 | Alper et al. ....................... 260/410.9 R |
| 5,144,068 | 9/1992 | Smith et al. ............................ 562/519 |
| 5,420,345 | 5/1995 | Smith ..................................... 562/519 |

FOREIGN PATENT DOCUMENTS 0 616 997   9/1994   European Pat. Off. .

*Primary Examiner*—Gary Geist
*Assistant Examiner*—Rosalynd Keys
*Attorney, Agent, or Firm*—Burns, Doane, Swecker & Mathis, L.L.P.

[57]          ABSTRACT

Preparation of carboxylic acids or corresponding esters by reacting an alcohol with carbon monoxide in the presence of an iridium catalyst and a halogen promoter. The reaction involves a reaction mixture composed of more than 0% to 10% water, more than 0% to 10% halogen promoter, 2% to 40% of an ester corresponding to the reaction of alcohol with the acid, soluble iodides in an amount such that the atomic ratio of iodides to iridium varies between more than 0 and 10, the carboxylic acid being used as the reaction solvent.

21 Claims, No Drawings

PROCESS FOR THE PREPARATION OF CARBOXYLIC ACIDS OR THE CORRESPONDING ESTERS IN THE PRESENCE OF A SOLUBLE CATALYST BASED ON IRIDIUM AND IODIDES

This application claims the benefit of priority under 35 U.S.C. § 365 to International Application No. PCT/FR95/00625 filed on May 15, 1995.

The present invention concerns a process for the preparation of carboxylic acids or the corresponding esters by carbonylation of an alcohol in the liquid phase in the presence of an iridium based catalyst.

The production of carboxylic acids, more particularly acetic acid, by reacting carbon monoxide with an alcohol such as methanol in the presence of a homogeneous catalyst is a well known process and has formed the subject matter of numerous patents and articles. Examples of catalysts which can be used in this type of reaction are cobalt, rhodium and iridium catalysts.

Only carbonylation processes using rhodium based catalysts have formed the basis of new developments on the industrial scale. The most recent generations of these processes thus use rhodium, large quantities of soluble iodide salts stabilizing that metal and small quantities of water. They perform well and can attain rates for the carbonylation of methanol to acetic acid which are in excess of 10 mol/l.h..

The preparation of carboxylic acids catalysed by cobalt is not currently used in new operations as the reaction conditions are very severe as regards pressure and temperature. Despite these conditions, the results obtained as regards selectivity towards the acid formed are not very satisfactory compared with the imposed constraints.

The results obtained for processes which use iridium based catalysts are poor. Carbonylation rates are of the order of 2 to 4 mol/l.h of acid formed and the number of moles of iridium used in the reaction is very high. Such processes cannot satisfactorily be used on an industrial scale.

European patent EP-A-0 618 184 describes a process for the carbonylation of an alcohol such as methanol in the presence of a catalytic system based on iridium and a halogenated promoter. This process is an improvement over the process described above. It was found that by maintaining a particular composition of the reaction mixture, comprising up to 10% of water, alcohol and halogenated promoter and up to 40% of an ester corresponding to the alcohol and the acid, it was possible to attain carbonylation rates which were in excess of or equal to 10 mol/h.l of acid formed. Such carbonylation rates are comparable with those obtained using carbonylation processes which are catalysed by rhodium.

The aim of the present invention is to provide a process for the preparation of carboxylic acids by a carbonylation reaction with a suitable reactant which does not use a rhodium based catalyst and which has a productivity which is comparable to that obtained using that catalyst.

The invention thus provides a process for the production of carboxylic acids or their corresponding esters containing (n+1) carbon atoms, by reacting carbon monoxide with at least one alcohol containing n carbon atoms in the liquid phase, in the presence of a catalytic system based on an iridium compound and a halogenated promoter. The process of the invention is characterized in that during the reaction, the water content is maintained at a level which is in the range 0 (exclusive limit) to 10%, the halogenated promoter concentration is maintained at a level in the range 0 (exclusive limit) to 10%, the concentration of the ester corresponding to the carboxylic acid and alcohol is maintained at a level which is in the range 2% to 40%, and the concentration of soluble iodides is such that the atomic ratio of iodides to iridium is in the range 0 (exclusive limit) to 10, the carboxylic acid constituting the reaction solvent.

In the description below, unless otherwise indicated, the percentages indicated are expressed as percentages by weight with respect to the total weight of the reaction mixture.

We have surprisingly discovered that the process of the invention, carried out in the presence of an iridium based catalyst under the stable conditions defined above, performs far better than prior art processes which use such a catalyst. In addition, and this is an important factor, the process of the invention can attain rates of carbonylation of the alcohol to the carboxylic acid, expressed in moles, which are comparable to those obtained in processes which are catalysed by rhodium, using similar quantities of catalyst.

It should also be noted that the process of the invention is carried out in the presence of relatively small quantities of halogenated promoter. This has the advantage of reducing the quantity of promoter to be separated from the acid formed and of reducing the energy consumption required to recover the halogenated compound, also its specific consumption, i.e., consumption during continuous operation of the carbonylation process.

Further, for given water and ester contents, this measure can reduce the concentration of hydrogen acid corresponding to the halogen of the promoter in the medium. As a result, the corrosivity of the medium is reduced, meaning that the materials which are brought into contact with such a medium are easier to select and are cheaper.

Finally, it has been established that iridium used under such conditions is remarkably selective in that the quantity of by-products formed, such as propionic acid or formic acid, is very small.

The quantity of the two above acids which is formed during the reaction is generally less than 200 ppm of each acid.

Further aims and advantages of the present invention will become apparent from the following description.

As stated above, the carbonylation reaction of the invention is carried out in the presence of a catalytic system which is based on at least one iridium compound and a halogenated promoter.

Since the reaction is carried out in the liquid phase, the catalytic system is in the form of compounds which are soluble in the reaction mixture.

All iridium compounds which are soluble or which can be dissolved in the reaction medium under the operating conditions of the invention can be used. By way of non limiting example, metallic iridium, simple salts of that metal, oxides thereof or co-ordination complexes thereof are of particular use. Reference should be made to United States patent U.S. Pat. No. 3,772,380, which includes a list of such compounds, for more detail.

Preferably, simple iridium salts are used such as iridium halides, the halogen being selected from chlorine, bromine and, preferably, iodine.

Iridium oxides and soluble iridium co-ordination complexes are suitable for use in the invention. In this latter category, the most frequently used complexes are those with ligands selected from carbon monoxide or a carbon monoxide/halogen combination, the halogen being selected from chlorine, bromine or, more particularly, iodine. The use of soluble iridium complexes in which the ligands are selected from organophosphorous or organonitrogen compounds, for example, is not excluded.

These catalysts can be obtained using any method which is known to the skilled person.

However, in a particularly advantageous implementation, the catalytic solution is prepared from a carbonyl complex of iridium such as $Ir_4CO_{12}$, by bringing said compound into contact with hydriodic acid and/or a precursor of such acid, in the presence of a solvent.

Examples of precursors which can be used to liberate hydriodic acid are iodine, $C_1$–$C_{10}$ alkyl iodides, $C_1$–$C_{10}$ acyl iodides, or alkali metal iodides.

Any compound can be used as a solvent provided that it dissolves the hydriodic acid or its precursor and the iridium based compound obtained. More particularly, solvents are used, alone or as a mixture, which are selected from carboxylic acids or their corresponding esters obtained by the process of the invention, or water.

Contact is made at a total pressure in the range 1 to 10 bars, at a temperature which is at most the boiling point of said solvent under the contact conditions.

The operation can be carried out in air, in an inert gas or in carbon monoxide.

A further advantageous example of a method for the preparation of a catalytic solution which is suitable for carrying out the invention consists of bringing one or more iridium oxides, which may or may not be hydrated, into contact in the liquid phase with hydriodic acid or a compound which can liberate hydriodic acid. The hydriodic acid can be used in the form of a gas or a solution, more particularly an aqueous solution. It can also be used in the form of a precursor as described in the previous variation.

More particularly, the quantity of hydriodic acid is such that the ratio between the number of moles of hydriodic acid and the number of moles of iridium is between 1 and 100.

The process of the invention can be carried out in air, in an inert gas, or in carbon monoxide, the gases being alone or in combination.

Generally, the total concentration of iridium in the reaction medium in the process of the invention is in the range 0.1 mmol/l to 100 mmol/l.

In a particular implementation, the iridium concentration is between 0.5 mmol/l and 40 mmol/l, preferably between 1 mmol/l and 25 mmol/l.

The second constituent of the catalytic system is a halogenated promoter. This can be in the form of a halogen alone or combined with other elements such as hydrogen, a $C_1$–$C_{10}$ alkyl radical, a $C_1$–$C_{10}$ acyl radical or a $C_6$–$C_{10}$ aryl radical.

The halogen is generally selected from chlorine, bromine or iodine, the latter being preferred.

In a particular implementation of the invention, the promoter comprises hydrogen or a $C_1$–$C_{10}$ radical. More particularly, the promoter comprises the halogen and a $C_1$–$C_{10}$ radical.

Preferably, this implementation is carried out in the presence of a halogenated promoter in which the radical corresponds to that of the alcohol used as a reactant during the reaction of the invention.

The concentration of halogenated promoter in the medium is in the range 0 (exclusive limit) to 10%. In a variation, the halogenated compound concentration in the reaction medium is in the range 0.5% to 8%, preferably in the range 1% to 6%.

As mentioned above, the reaction of the invention is carried out in the presence of an alcohol comprising one less carbon atom than the carboxylic acid or corresponding ester which is produced.

Examples of reactants which can be used are saturated alcohols containing one to ten carbon atoms. Particular examples of such compounds are methanol, ethanol, propanol, butanol and 1,4-butanediol. These alcohols may be mono- or dihydroxylated.

In a preferred implementation, the alcohols are selected from monohydroxylated compounds.

It is important to note that the alcohol used as the reactant can be present in the reaction medium as it is or it can be masked. The alcohol can be present in the form of a halogenated derivative and/or an ether and/or an ester obtained by reaction between said alcohol and the carboxylic acid which is present.

The concentration of reactant in the reaction medium can vary between wide limits because of the different species in which the reactant can be present.

As a result, the concentration of the alcohol per se in the reaction medium can be in the range 0% to 10%.

Preferably, the medium has an alcohol concentration which is in the range 0.1% to 8%.

The other reactant which is necessary for the production of a carboxylic acid is carbon monoxide. This can be used in its pure form or it can be diluted in a gas such as hydrogen, methane, carbon dioxide or any other type of gas, for example nitrogen.

In a particular implementation of the invention, carbon monoxide is used which is present in a purity of at least 99%.

The partial pressure of the carbon monoxide is normally in the range 5 to 200 bar, more particularly between 5 and 100 bar. Preferably, the partial pressure of carbon monoxide is in the range 10 to 50 bar. It should be noted, however, that partial pressures which are outside these ranges can be envisaged.

The carbonylation reaction of the invention is also carried out in the presence of water. More particularly, the water content in the reaction medium is in the range 0% (exclusive limit) to 10%.

In one particular implementation of the process of the invention, the water content in the medium is in the range 0.5% to 8%, preferably in the range 2% to 8%.

In addition to the compounds and reactants mentioned above, the process of the invention is carried out in the presence of esters, preferably corresponding to the reaction of the alcohol used in the reaction with the carboxylic acid present in the reaction medium.

More particularly, the concentration of ester in the medium is in the range 2% to 40%. In a particular implementation of the invention, the ester concentration is in the range 5% to 30%.

The process of the invention is carried out in a solvent which preferably corresponds to the carboxylic acid formed by the reaction.

Finally, the process of the invention is carried out in the presence of iodides which are soluble in the reaction medium. The iodides can be introduced as they are into the reaction medium and also in the form of compounds which can form soluble iodides.

The term "iodides" means ionic species, i.e., not containing any covalent iodides (in particular the halogenated promoter) nor containing hydriodic acid.

Thus the iodides introduced into the mixture are selected from inorganic or organic iodides.

Examples of inorganic iodides are alkaline-earth or alkali metal iodides, the latter being preferred. Examples are potassium iodide, lithium iodide, and sodium iodide.

Examples of organic iodides are organic compounds containing at least one organophosphorous group and/or at least one organonitrogen group which react with iodine based compounds to produce ionic species containing that halogen. Examples are triphenyl phosphonium iodide and N-methyltriethyl ammonium iodide.

Examples of compounds which can form stable iodides in the reaction medium are alkaline-earth or alkali metal carboxylates and hydroxides, in particular lithium acetate, potassium hydroxide and sodium hydroxide.

It should also be noted that the iodides can have origins other than those indicated above.

Thus these compounds may result from impurities such as the alkali or alkaline-earth metals present in the starting materials used to prepare the catalytic solution.

The iodides may also originate from corrosive metals appearing during the carbonylation reaction. It is preferable to maintain the threshold concentration of these metals at a relatively low level, of the order of several hundreds of parts per million, as they encourage the water gas reaction and increase the iodide/iridium atomic ratio.

One important characteristic of the process of the invention consists of introducing a particular quantity of iodide, which quantity depends on the quantity of iridium present, into the medium. The quantity of iodides introduced is such that the atomic ratio of iodides introduced to iridium (expressed in mole/mole) is in the range 0 (exclusive limit) to 10. This ratio is maintained within this range during the reaction.

In a preferred implementation of the invention, the iodide/iridium atomic ratio is maintained in the range 0 (exclusive limit) to 3. More particularly, the ratio is in the range 0 (exclusive limit) to 1.5.

It has been found that addition of such quantities of iodides improves the stability of the catalyst and keeps the productivity of the process high.

Thus as indicated above, the present invention consists of keeping water, the halogenated promoter, the ester, iodides and carboxylic acid in the reaction medium in the proportions which have been defined.

As a result, the present invention is particularly intended to be carried out continuously and the stable operating conditions of the process correspond to the indicated composition and proportions.

More particularly, concerning the soluble iodides, the soluble iodide/iridium atomic ratio can be maintained by treating the mixture containing at least one iridium compound with an ion exchange resin then adding the iodides in soluble form in a quantity such that the atomic ratio in the reaction medium is in the range 0 (exclusive limit) to 10.

In a first variation of the invention, a mixture which is the catalytic solution is treated. The term "catalytic solution" means the solution comprising an iridium compound in the presence of appropriate solvent(s) or reactant(s).

In a second variation, the mixture to be treated is the reaction mixture to which the soluble iodides have not yet been added.

In a third variation, the mixture to be treated corresponds to the reaction mixture during the carbonylation reaction or after it has been stopped. Thus, more particularly, the mixture to be treated can be at least a portion of the liquid stream from partial vaporization of the reaction mixture.

It should be remembered that the carbonylation process of the invention can be carried out in installations which employ conventional processes. These latter usually consist of three zones. The first zone is the reaction zone, comprising a pressurized reactor; the second zone is a zone for separating the acid or ester formed by partial vaporization of the reaction mixture. The vaporized portion is then sent to a third zone for purification of the carboxylic acid or corresponding ester; the remaining portion of the mixture, in liquid form, mainly comprising the catalyst, is recycled to the reactor.

Combinations of the above variations can, of course, be envisaged.

The mixture may or may not be treated in a single step. Thus the entire mixture can be treated with the resin. This is particularly the case where the mixture is the catalytic solution. This type of operation is generally carried out batchwise. It is also possible to remove a portion of the mixture and treat that stream in accordance with the invention, either continuously or batchwise. This is preferable when the carbonylation reaction is carried out simultaneously with the resin treatment.

Suitable resins for use in the process of the invention are cationic exchange resins which may be strong acid types or weak acid types, in their hydrogen form.

Examples of weak acid resins are resins are copolymers of acrylic acid, methacrylic acid, and the corresponding esters or nitrites. Phenolic resins can also be used.

Particular examples of strong acid resins are resins which are styrene-divinylbenzene copolymers with grafted sulphonated functional groups. Resins of this type are sold under the trade name DOWEX by Dow, under the trade name PUROLITE by Purolite, or under the trade name AMBERLYST by Rohm & Haas.

In a preferred implementation, strong acid type resins are used.

The resins can be used in gel form or in macroporous form.

In particular, the mixture is treated on a fixed bed.

The temperature at which the mixture is brought into contact with the resin is in the range 10° C. to 150° C., more particularly in the range 20° C. to 100° C.

Once the mixture has been treated, the iodide ions or their precursor are added to obtain an iodide/iridium atomic ratio in the reaction mixture which is within the ranges given above.

Addition can be made to the newly treated mixture but it can also be made to the reaction mixture in general, i.e., at any point in the process where the reaction mixture exists.

Thus the iodides or their precursor can be added at any point in the reaction zone or in the separation zone.

As the reaction is started, the various components are introduced into a suitable reactor provided with sufficient stirring means to ensure gas-liquid transfer. It should be noted that if, as is preferable, the reactor contains mechanical stirring means for the reaction mixture, operating without such means is not excluded; the mixture may be homogenised on introduction of carbon monoxide into the reactor.

There is no order of preference for the introduction of the components into the reaction medium, whether they are in their final form and/or in the form of one or more precursors.

In a first variation of the invention, the halogenated promoter described above is introduced as it is into the reaction mixture.

In a second variation of the invention, the promoter is introduced in the form of at least one precursor.

In this case, the precursor is generally in the form of a compound which can liberate the radical of the halogenated promoter defined above into the reaction medium. This occurs by reaction of the precursor with a halogen, its corresponding hydrogen acid, and/or an iodide: these compounds are present in the medium or introduced for this purpose.

Non limiting examples of suitable precursors are compounds selected from alcohols with formula (1) ROH; ethers with formula (2) ROR' or esters with formula (3) R'COOR, which are used alone or as a mixture. In these formulae, radicals R and R', which may be identical or different, each represent a $C_1$–$C_{10}$ alkyl radical, a $C_1$–$C_{10}$ acyl radical, or a $C_6$–$C_{10}$ aryl radical: radical R is the radical of the halogenated promoter.

Thus methanol, ethanol, propanol, butanol, dimethyl ether, diethyl ether, ethylene oxide and methyl acetate are suitable precursors for the halogenated promoter.

The carbonylation reaction is normally carried out at a temperature which is in the range 150° C. to 250° C. Preferably, the reaction temperature is in the range 180° C. to 210° C.

In a particular implementation of the process of the invention, the reaction mixture is regularly purged of corrosive metals contained therein, in particular iron, molybdenum, chromium, and nickel. This operation is carried out using any means which is known to the skilled person, such as treatment of the reaction mixture using an ion exchange resin or by precipitation of the catalyst and separation thereof from the corrosion metals by filtering.

The process of the invention is suitable for the manufacture of any type of carboxylic acid or corresponding ester, containing a minimum of two carbon atoms. Thus it can be used to prepare propionic acid from ethanol, succinic acid from ethylene oxide, adipic acid from 1,4-butanediol, or the corresponding esters of these acids.

However, the process is particularly suitable for the production of acetic acid and/or methyl acetate from methanol.

In a preferred implementation, the process of the invention is carried out using methyl iodide, methyl acetate, soluble iodides and acetic acid as the solvent in addition to methanol.

Some non limiting examples will now be described.

EXAMPLES 1 AND 2

Carbonylation tests were carried out in continuous mode in a 300 $cm^3$ autoclave provided with a mechanical stirring means and means for introducing the reactants.

The catalytic solution was obtained from $Ir_4CO_{12}$ and was prepared as follows:

10 g of $Ir_4CO_{12}$, 50 g of 57% hydriodic acid dissolved in water and 290 g of acetic acid were introduced into a glass flask.

The mixture was heated under reflux for 4 hours, with stirring, in air.

Introduction of methanol, methyl iodide, methyl acetate and water was regulated so that the concentrations of the different components in the reaction medium were as indicated in the table below.

The residence time in the reactor was about 10 minutes.

The total pressure in the autoclave was 30 bar and the temperature was kept at 190° C.

The reaction mixture was degassed and cooled at the autoclave outlet.

The mixture and the gases were analysed by gas phase chromatography.

| Example | $H_2O$ | $CH_3CO_2CH_3$ | $CH_3I$ | LiI | Ir | Li/Ir | $V_{carb}$ |
|---|---|---|---|---|---|---|---|
| 1 | 9.5 | 23 | 1.3 | 33 | 1200 | 0.7 | 8.5 |
| 2 | 5.8 | 13 | 4 | 61 | 1760 | 0.96 | 9.1 |

The concentrations of water, methyl acetate and methyl iodide are expressed as % by weight with respect to the total weight of the reaction mixture, the complement to 100% being provided by acetic acid.

The lithium iodide and iridium concentrations are expressed in ppm.

$V_{carb}$ represents the rate of carbonylation, expressed in mol/l.h..

This was obtained by measuring the rate of consumption of CO, taking into account the quantity of gas used for the formation of $CO_2$.

EXAMPLE 3

50 ml of a reaction mixture from a carbonylation reaction, containing mainly acetic acid, a soluble iridium complex (1800 ppm of iridium), methyl iodide, methyl acetate, methanol, water and 51 ppm of lithium in the form of the soluble iodide, was treated in a 2.7 cm diameter column of 25 cm length containing 26 ml of DOWEX C-500 resin.

Before use, the resin had been successively washed with water and isopropanol to eliminate any organic pollutants present in the commercial product and it had been immersed for 24 hours in an acetic acid solution to allow it to swell to its maximum amount.

The reaction mixture was supplied to the head of the column at ambient temperature at atmospheric pressure. The solution obtained from the foot of the column was returned to the head to contact it again with the resin. The treatment was continued for 4 hours to reach adsorption equilibrium.

After treatment, the solution was recovered for analysis. Atomic absorption measurements indicated that 0.2 ppm of lithium remained in the solution in the form of the soluble iodide, corresponding to an adsorption yield of 97.3%.

It was established that the iridium had not been adsorbed by the resin.

EXAMPLE 4

The procedure of the preceding example was followed, but the reaction mixture was treated using PUROLITE C 100 resin.

Atomic absorption analysis of the recovered solution showed that 0.45 ppm of lithium remained in the form of the soluble iodide, corresponding to an adsorption yield of 94%.

The iridium had not been adsorbed by the resin.

EXAMPLE 5

50 ml of a reaction mixture from a carbonylation reaction, containing mainly acetic acid, a soluble iridium complex (2100 ppm of iridium), methyl iodide, methyl acetate, methanol, water and 245 ppm of potassium in the form of the soluble iodide, was treated.

The procedure of Example 1 was followed.

Atomic absorption analysis of the recovered solution showed that 0.3 ppm of potassium remained in the form of the soluble iodide, corresponding to an adsorption yield of more than 99%.

The iridium had not been adsorbed by the resin.

EXAMPLE 6

The procedure of the preceding example was followed, but the reaction mixture was treated using PUROLITE C 100 resin.

Analysis showed that 3.8 ppm of potassium remained as the soluble iodide, corresponding to an adsorption yield of 97%. The iridium had not been adsorbed.

EXAMPLE 7

A catalytic iridium solution, containing 16500 ppm of iridium, 76 ppm of sodium in the form of the soluble iodide and 7 ppm of potassium in the form of the soluble iodide, was treated.

The treatment was carried out by passage through AMBERLYST 16 resin (Rohm & Haas) using the operating procedure described in the preceding examples.

The volume of resin used was of the order of 10 ml and the volume of solution treated was of the order of 630 ml.

The results show that 5 ppm of sodium remained, corresponding to an adsorption yield of 93%, and 2 ppm of potassium remained, corresponding to a yield of 70%.

We claim:

1. A process for the preparation of carboxylic acids or their corresponding esters, said process comprising the step of:

contacting at least one alcohol with carbon monoxide, in the liquid phase, in a reaction mixture comprising water, an ester, a carboxylic acid, iodides, and a catalyst system comprising an iridium compound and a halogenated promoter at conditions effective to produce carboxylic acids or their corresponding esters, said reaction mixture comprising:

(a) a water content of greater than 0 up to 10%;

(b) a halogenated promoter concentration of greater than 0 up to 10%;

(c) an ester concentration of 2% to 40%; and (d) an atomic ratio of iodides to iridium of greater than 0 up to 10.

2. The process according to claim 1, wherein the atomic ratio of iodides to iridium ranges from greater than 0 to 3.

3. The process according to claim 2, wherein the atomic ratio of iodides to iridium ranges from greater than 0 to 1.5.

4. The process according to claim 1, wherein said iodides are selected from alkali metal iodides, organophosphorus iodides, and organonitrogen iodides.

5. The process according to claim 1, wherein the water content ranges from 0.5 to 8%.

6. The process according to claim 1, wherein the halogenated promoter concentration ranges from 0.5 to 8%.

7. The process according to claim 1, wherein the ester concentration ranges from 5 to 30%.

8. The process according to claim 1, wherein said at least one alcohol is a saturated $C_1$–$C_{10}$ hydrocarbon alcohol.

9. The process according to claim 1, wherein said halogenated promoter comprises chlorine, bromine, or iodine in combination with hydrogen, a $C_1$–$C_{10}$ alkyl radical, a $C_1$–$C_{10}$ acyl radical, or a $C_1$–$C_{10}$ aryl radical.

10. The process according to claim 8, wherein said halogenated promoter comprises a radical corresponding to that of said alcohol.

11. The process according to claim 1, wherein acetic acid is prepared by reacting methanol with carbon monoxide in the presence of water, methyl iodide, methyl acetate, alkali metal iodides, and acetic acid.

12. A process for the preparation of carboxylic acids or their corresponding esters, said process comprising the step of:

contacting at least one alcohol with carbon monoxide, in the liquid phase, in a reaction mixture comprising water, an ester, a carboxylic acid, iodides, and a catalyst system comprising an iridium compound and a halogenated promoter at conditions effective to produce carboxylic acids or their corresponding esters, said reaction mixture comprising:

(a) a water content of greater than 0 up to 10%;

(b) a halogenated promoter concentration of greater than 0 up to 10%;

(c) an ester concentration of 2% to 40%; and (d) an atomic ratio of iodides to iridium of greater than 0 up to 10, wherein the atomic ratio of iodides to iridium is maintained by the following steps:

treating a mixture comprising at least the iridium compound with an ion exchange resin; and adding soluble iodides in a quantity such that the atomic ratio of iodides to iridium in the reaction mixture is in the range of greater than 0 up to 10.

13. The process according to claim 11, wherein said treated mixture is a catalytic solution.

14. The process according to claim 11, wherein said treated mixture is the reaction mixture before introduction of the soluble iodides.

15. The process according to claim 11, wherein said treated mixture is the reaction mixture.

16. The process according to claim 11, wherein the ion exchange resin is a strong acid type or a weak acid type cationic exchange resin in its hydrogen form.

17. The process according to claim 11, wherein the ion exchange resin is a styrene-divinylbenzene copolymer resin containing grafted sulfonated functional groups.

18. The process according to claim 11, wherein said at least one alcohol is a saturated $C_1$–$C_{10}$ hydrocarbon alcohol.

19. The process according to claim 11, wherein said halogenated promoter comprises chlorine, bromine, or iodine in combination with hydrogen, a $C_1$–$C_{10}$ alkyl radical, a $C_1$–$C_{10}$ acyl radical, or a $C_1$–$C_{10}$ aryl radical.

20. The process according to claim 19, wherein said halogenated promoter comprises a radical corresponding to that of said alcohol.

21. The process according to claim 11, wherein acetic acid is prepared by reacting methanol with carbon monoxide in the presence of water, methyl iodide, methyl acetate, alkali metal iodides, and acetic acid.

* * * * *

UNITED STATES PATENT AND TRADEMARK OFFICE
CERTIFICATE OF CORRECTION

PATENT NO. : 5,773,642
DATED : June 30, 1998
INVENTOR(S) : Philippe Denis et al.

It is certified that error appears in the above-identified patent and that said Letters Patent is hereby corrected as shown below:

Please correct the dependency of claims 13-19 and 21 as follows:

Claim 13,
Line 1, change "11" to --12--.

Claim 14,
Line 1, change "11" to --12--.

Claim 15,
Line 1, change "11" to --12--.

Claim 16,
Line 1, change "11" to --12--.

Claim 17,
Line 1, change "11" to --12--.

Claim 18,
Line 1, change "11" to --12--.

Claim 19,
Line 1, change "11" to --12--. and

Claim 21,
Line 1, change "11" to --12--.

Signed and Sealed this

Third Day of July, 2001

*Attest:*

Nicholas P. Godici

*Attesting Officer*

NICHOLAS P. GODICI
*Acting Director of the United States Patent and Trademark Office*